(12) United States Patent
Kamath

(10) Patent No.: US 12,310,638 B2
(45) Date of Patent: May 27, 2025

(54) MODULAR BONE REINFORCEMENT

(71) Applicant: Atul F. Kamath, Solon, OH (US)

(72) Inventor: Atul F. Kamath, Solon, OH (US)

(*) Notice: Subject to any disclaimer, the term of this patent is extended or adjusted under 35 U.S.C. 154(b) by 497 days.

(21) Appl. No.: 17/739,641

(22) Filed: May 9, 2022

(65) Prior Publication Data

US 2022/0354553 A1 Nov. 10, 2022

Related U.S. Application Data

(60) Provisional application No. 63/235,333, filed on Aug. 20, 2021, provisional application No. 63/185,536, filed on May 7, 2021.

(51) Int. Cl.
  *A61B 17/80* (2006.01)
  *A61B 17/00* (2006.01)
  (Continued)

(52) U.S. Cl.
  CPC ............. *A61B 17/8085* (2013.01); *A61B 2017/00477* (2013.01); *A61B 2017/564* (2013.01);
  (Continued)

(58) Field of Classification Search
  CPC .............. A61F 2/30734; A61F 2/34; A61F 2002/30153; A61F 2002/30154; A61F 2002/30156; A61F 2002/30383; A61F 2002/305; A61F 2002/30604; A61F 2002/30607; A61F 2002/30616; A61F 2002/30736; A61F 2002/30772; A61F 2002/30818; A61F 2002/30985; A61F 2002/342; A61F 2002/343; A61F 2002/3425; A61F 2002/348; A61B 17/8085; A61B 17/8095; A61B 17/8061; A61B 17/80; A61B 17/8071; A61B 17/8076; A61B 17/8066; A61B 2017/00477; A61B 2017/564; B33Y 80/00
  (Continued)

(56) References Cited

U.S. PATENT DOCUMENTS

| 4,681,589 A | 7/1987 | Tronzo |
| 5,326,368 A | 7/1994 | Collazo |

(Continued)

FOREIGN PATENT DOCUMENTS

| WO | 2007082810 A2 | 7/2007 |
| WO | 2013067528 A1 | 5/2013 |

*Primary Examiner* — Marcela I. Shirsat
(74) *Attorney, Agent, or Firm* — MacMillan, Sobanski and Todd, LLC

(57) ABSTRACT

Modular bone reinforcement systems, bone plates, assembled bone reinforcements, and methods of reinforcing a bone are described. A modular bone reinforcement system includes a plurality of bone plates, each of which has a series of tabs disposed along at least one edge of the bone plate for forming a snap-fit attachment to a mating series of tabs of another bone plate of the plurality of bone plates to form an assembled bone reinforcement. A first bone plate of the plurality of bone plates has a first shape and a second bone plate of the plurality of bone plates has a second shape that is different from the first shape. The modular bone reinforcement system can include additional components, such one or more fixation devices, reduction devices, navigation aids, or other components.

16 Claims, 13 Drawing Sheets

(51) Int. Cl.
    *A61B 17/56* (2006.01)
    *A61F 2/30* (2006.01)
    *A61F 2/34* (2006.01)
(52) U.S. Cl.
    CPC ....... *A61B 17/8061* (2013.01); *A61B 17/8066* (2013.01); *A61F 2002/30154* (2013.01); *A61F 2002/30156* (2013.01); *A61F 2002/30383* (2013.01); *A61F 2002/305* (2013.01); *A61F 2/30734* (2013.01); *A61F 2002/30736* (2013.01); *A61F 2002/342* (2013.01); *A61F 2002/3425* (2013.01); *A61F 2002/348* (2013.01)
(58) Field of Classification Search
    USPC .......................................................... 606/71
    See application file for complete search history.

(56) References Cited

U.S. PATENT DOCUMENTS

| | | | |
|---|---|---|---|
| 5,549,692 A | 8/1996 | Hauser et al. | |
| 5,871,548 A * | 2/1999 | Sanders | A61F 2/34 623/22.36 |
| 5,931,870 A | 8/1999 | Cuckler et al. | |
| 6,004,353 A | 12/1999 | Masini | |
| 6,162,257 A * | 12/2000 | Gustilo | A61B 17/1666 623/22.32 |
| 6,416,553 B1 * | 7/2002 | White | A61F 2/4637 623/22.38 |
| 6,454,809 B1 * | 9/2002 | Tornier | A61F 2/30724 623/22.32 |
| 7,867,261 B2 | 1/2011 | Sixto, Jr. et al. | |
| 7,993,408 B2 | 8/2011 | Meridew et al. | |
| 9,005,302 B2 | 4/2015 | Brehm | |
| 9,014,835 B2 | 4/2015 | Azernikov et al. | |
| 9,101,428 B2 | 8/2015 | Long et al. | |
| 9,186,257 B2 | 11/2015 | Geisler et al. | |
| 10,159,475 B2 | 12/2018 | Frey et al. | |
| 2008/0021568 A1 | 1/2008 | Tulkis et al. | |
| 2008/0077133 A1 | 3/2008 | Schulze | |
| 2008/0172130 A1 | 7/2008 | Macara | |
| 2009/0204225 A1 | 8/2009 | Meridew et al. | |
| 2012/0316562 A1 | 12/2012 | Costa | |
| 2013/0035766 A1 * | 2/2013 | Meridew | A61F 2/34 623/22.21 |
| 2013/0338786 A1 * | 12/2013 | Haidukewych | A61M 5/31596 623/22.32 |
| 2018/0146994 A1 | 5/2018 | Biedermann | |

\* cited by examiner

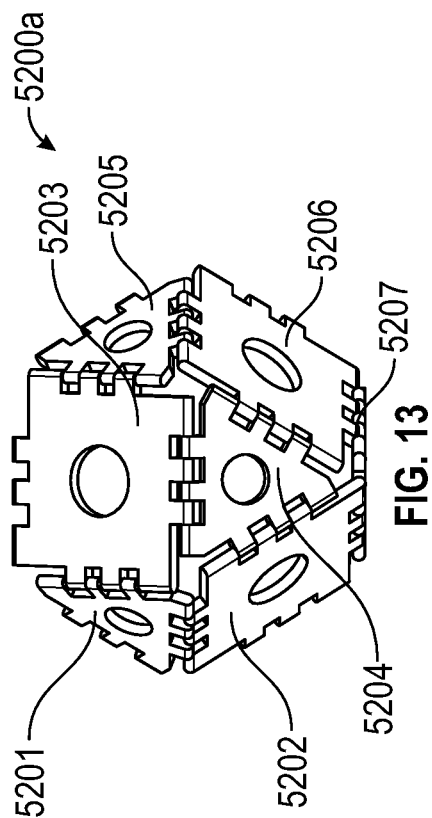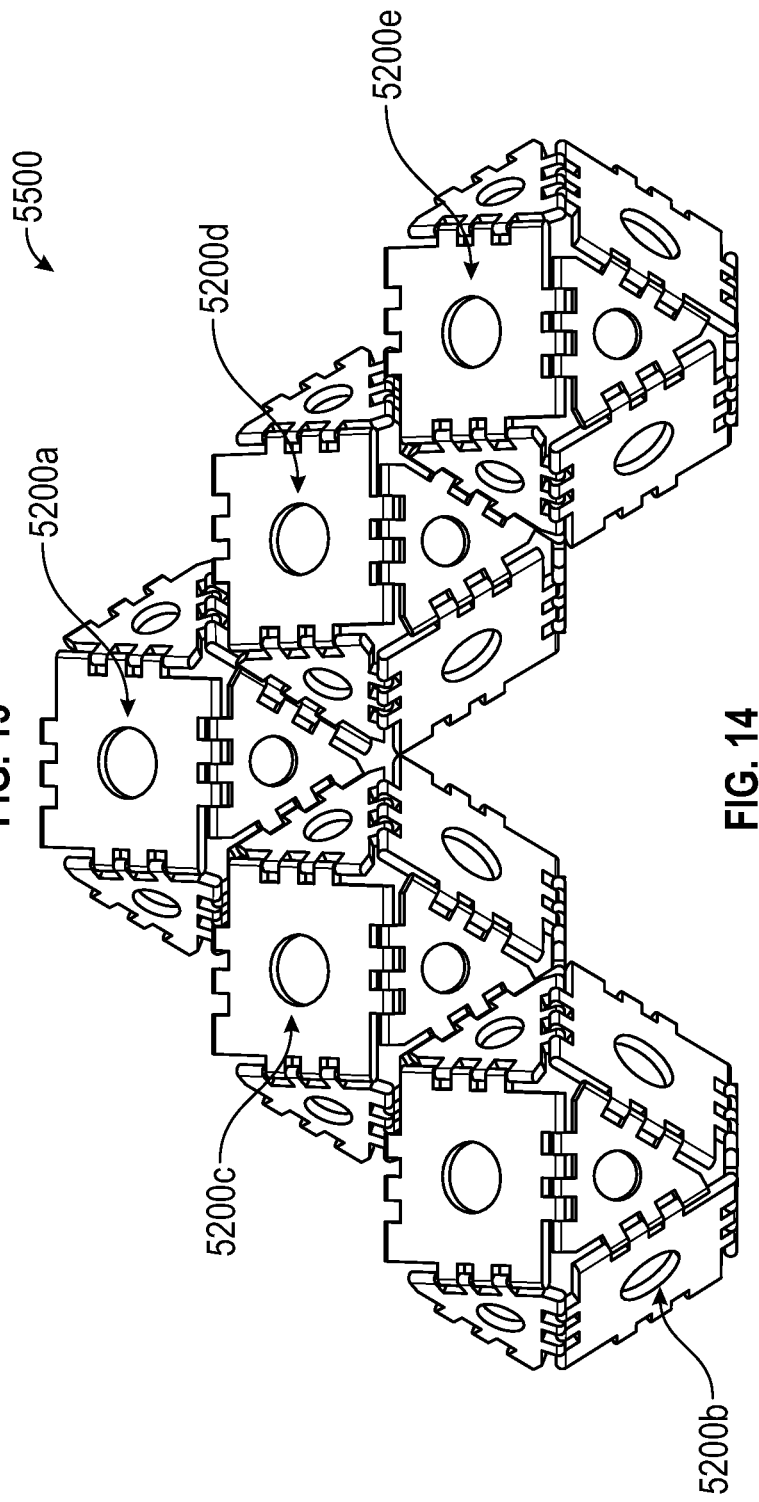

MODULAR BONE REINFORCEMENT

RELATED APPLICATIONS

This application claims priority to U.S. Provisional Application No. 63/185,536, filed May 7, 2021, and U.S. Provisional Application No. 63/235,333, filed Aug. 20, 2021. The entire contents of each of these related applications are hereby incorporated by reference into this disclosure.

FIELD

The disclosure relates to the field of medical devices. More particularly, the disclosure relates to modular bone reinforcement systems, bone plates, and bone reinforcements useful in a variety of clinical applications. Specific examples relate to modular bone reinforcement systems, bone plates, assembled bone reinforcements, such as acetabular cups and attached extensions useful in revision hip surgery, and methods of reinforcing a bone.

BACKGROUND

Both primary and revision orthopedic surgeries often require complex reconstruction efforts using bone reinforcement systems, bone plates, and assembled bone reinforcements. While many reinforcement devices and systems are known, conventional products are often inadequate for reconstruction in environments presenting irregular bone shapes and/or complex surfaces. A need exists, therefore, for new and improved bone reinforcement systems, bone plates, bone reinforcements, and methods of reinforcing a bone.

SUMMARY OF SELECTED EXAMPLES

Various modular bone reinforcement systems are described.

An example modular bone reinforcement system includes a plurality of bone plates, each of which has a series of tabs disposed along at least one edge of the bone plate for forming a snap-fit attachment to a mating series of tabs of another bone plate of the plurality of bone plates to form an assembled bone reinforcement.

Another example modular bone reinforcement system includes a plurality of bone plates, each of which has a series of tabs disposed along at least one edge of the bone plate for forming a snap-fit attachment to a mating series of tabs of another bone plate of the plurality of bone plates to form an assembled bone reinforcement. A first bone plate of the plurality of bone plates has a first shape and a second bone plate of the plurality of bone plates has a second shape that is different from the first shape.

Another example modular bone reinforcement system includes a plurality of bone plates and a reduction and/or fixation device, such as a bone screw. Each of the bone plates has a series of tabs disposed along at least one edge of the bone plate for forming a snap-fit attachment to a mating series of tabs of another bone plate of the plurality of bone plates to form an assembled bone reinforcement.

Various example bone plates are described.

An example bone plate has a main body having a square shape defining first, second, third, and fourth edges, each of which defines a series of tabs. The main body has an upper surface and an opposing lower surface and defines a plurality of passageways, each of which extends through the entire thickness of the main body from the upper surface to the lower surface.

Another example bone plate has a main body having a triangular shape defining first, second, and third edges, each of which defines a series of tabs.

Various example assembled bone reinforcements are described.

An example assembled bone reinforcement includes a plurality of bone plates attached in series. Each bone plate of the plurality of bone plates defines a series of tabs on each edge of the individual bone plate. Adjacent pairs of bone plates of the plurality of bone plates are attached to each other through a snap-fit attachment formed by interlocking the series of tabs of the adjacent bone plates.

Another example assembled bone reinforcement includes a plurality of bone plates attached in series. Each bone plate of the plurality of bone plates defines a series of tabs on each edge of the individual bone plate. Adjacent pairs of bone plates of the plurality of bone plates are attached to each other through a snap-fit attachment formed by interlocking the series of tabs of the adjacent bone plates. The assembled bone reinforcement includes a cup portion and an extension portion that extends away from a peripheral edge of cup portion.

Various example methods of reinforcing a bone are described.

An example method of reinforcing a bone comprises attaching a first bone plate of a modular bone reinforcement system according to an embodiment to a second bone plate of the modular bone reinforcement system to form an assembled bone reinforcement; and attaching the assembled bone reinforcement to a bone of a patient, such as a bone of a human being or other animal. An optional step comprises rotating one or both of the first and second bone plates about an axis extending through the attachment formed between the interlocking series of tabs of the first and second attached bone plates.

Another example method of reinforcing a bone comprises attaching a first bone plate of a modular bone reinforcement system according to an embodiment to a bone of a patient, such as a bone of a human being; attaching a second bone plate of the modular bone reinforcement system to the first bone plate to form an assembled bone reinforcement; and attaching the second bone plate to the bone. An optional step comprises rotating the second bone plate about an axis extending through the attachment formed between the interlocking series of tabs of the first and second attached bone plates.

Additional understanding of the example modular bone reinforcement systems, bone plates, and assembled bone reinforcements can be obtained by review of the detailed description, below, and the appended drawings.

BRIEF DESCRIPTION OF THE DRAWINGS

FIG. 13 is a perspective view of another example assembled bone reinforcement.

FIG. 14 is a perspective view of another example assembled bone reinforcement that includes the assembled bone reinforcement illustrated in FIG. 13.

DETAILED DESCRIPTION OF SELECTED EXAMPLES

The following detailed description and the appended drawings describe and illustrate various example modular bone reinforcement systems, bone plates, and assembled bone reinforcements. The description and illustration of these examples are provided to enable one skilled in the art to make and use an example modular bone reinforcement system, bone plate, and assembled bone reinforcement according to an embodiment. They are not intended to limit the scope of the claims in any manner.

Figure 1:
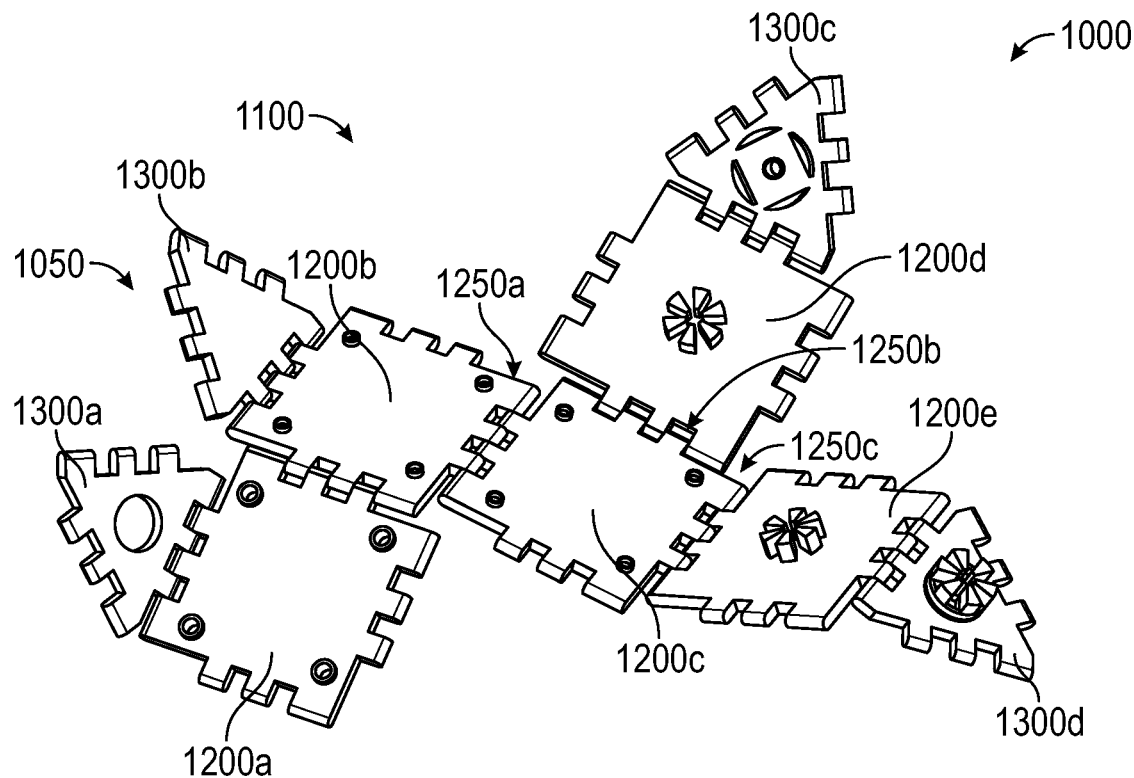
FIG. 1 is a perspective view of an example modular bone reinforcement system. The modular bone reinforcement system is illustrated as an assembled bone reinforcement in a first configuration.
Figure 2:
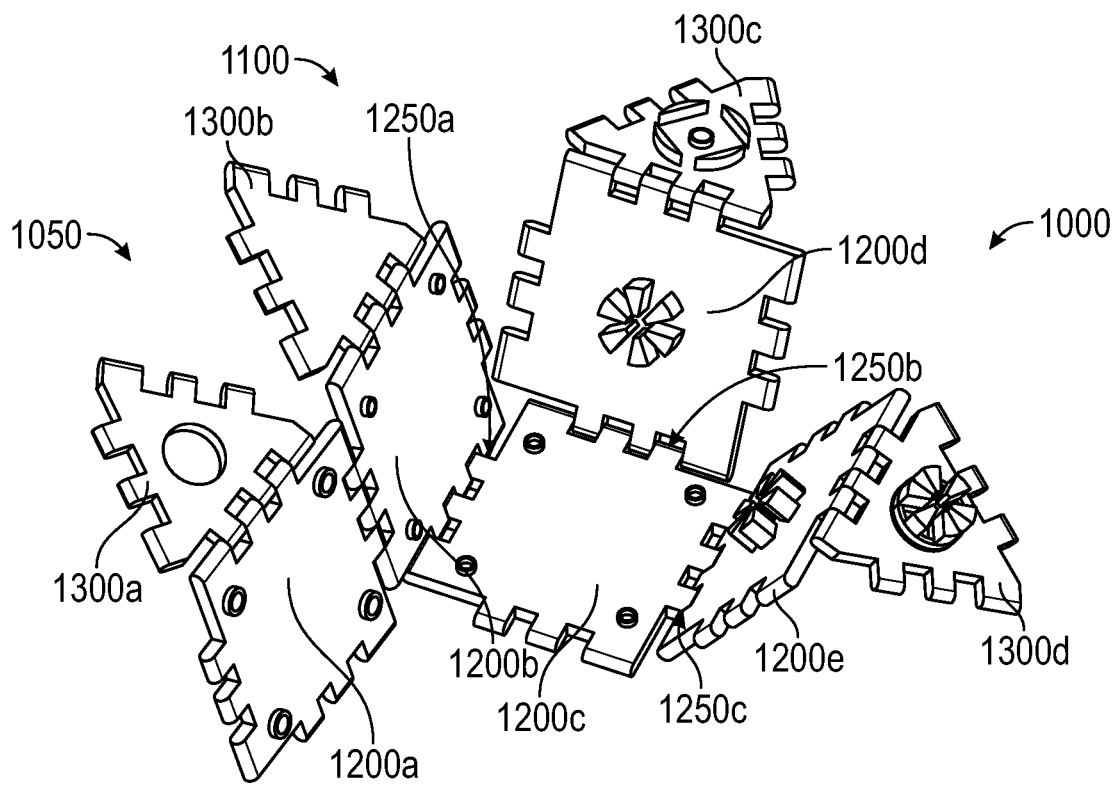
FIG. 2 is another perspective view of the example modular bone reinforcement system illustrated in FIG. 1. The modular bone reinforcement system is illustrated as an assembled bone reinforcement in a second configuration.
Figure 3:
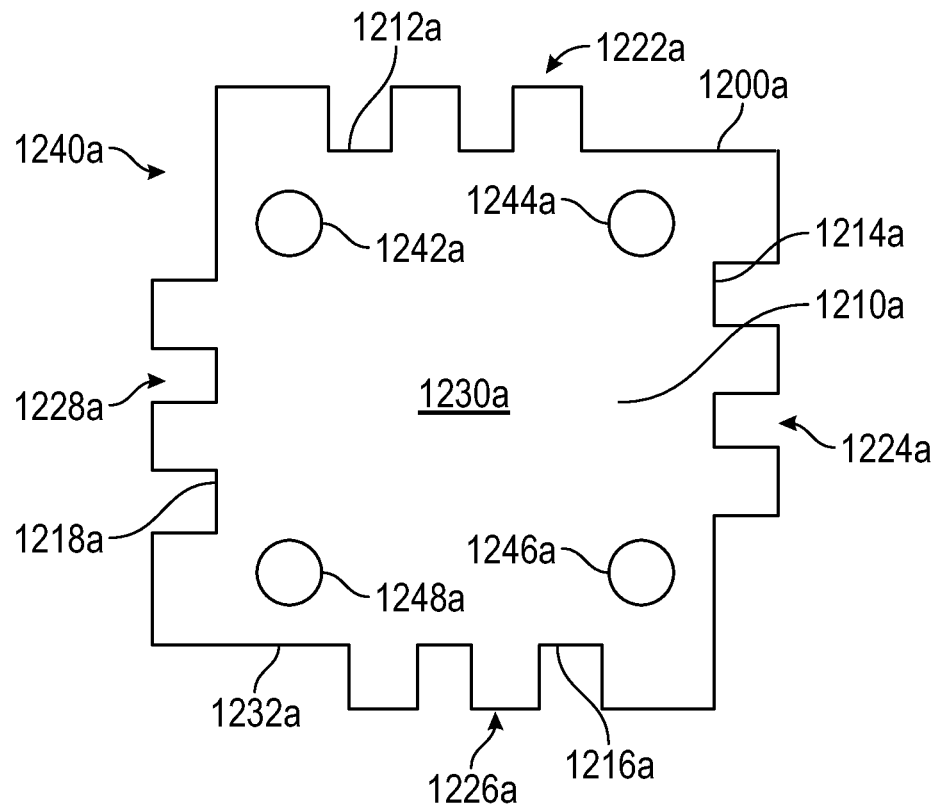
FIG. 3 is a perspective view of an example bone plate. The bone plate is a component of the example modular bone reinforcement system illustrated in FIG. 1.
Figure 4:
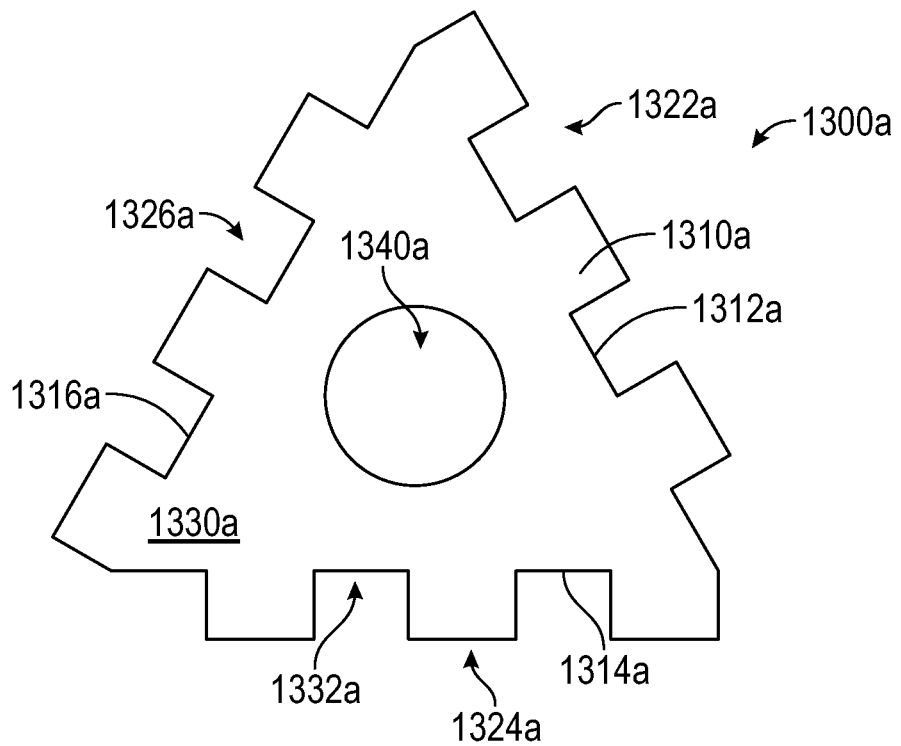
FIG. 4 is a perspective view of another example bone plate. The bone plate is a component of the example modular bone reinforcement system illustrated in FIG. 1.
Figure 5:
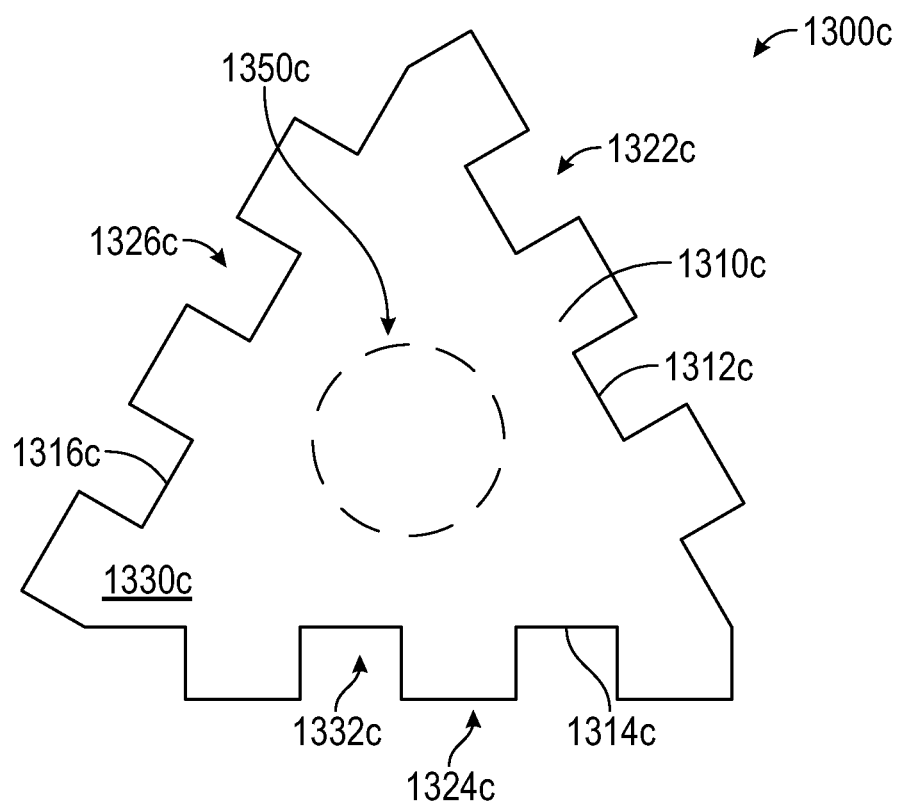
FIG. 5 is a perspective view of another example bone plate. The bone plate is a component of the example modular bone reinforcement system illustrated in FIG. 1.

FIGS. 1 and 2 illustrate an example modular bone reinforcement system 1000. Modular bone reinforcement system 1000 includes a plurality of individual bone plates 1200a, 1200b, 1200c, 1200d, 1200e, 1300a, 1300b, 1300c, 1300d, each of which has a generally planar structure and includes at least one series of tabs configured to form a snap-fit attachment with a series of tabs of one or more other bone plates 1200a, 1200b, 1200c, 1200d, 1200e, 1300a, 1300b, 1300c, 1300d of the modular bone reinforcement system 1000. As used herein, the term "modular bone reinforcement system" refers to a collection of two or more individual bone plates according to an embodiment of the invention; the term "assembled bone reinforcement" refers to a collection of two or more bone plates according to an embodiment of the invention and having snap-fit connections between an individual pair or between multiple pairs of bone plates of the collection. Thus, in FIGS. 1 and 2, the modular bone reinforcement system 1000 is illustrated as an assembled bone reinforcement 1050. FIG. 1 illustrates the assembled bone reinforcement 1050 in a first configuration; FIG. 2 illustrates the assembled bone reinforcement 1050 in a second configuration. FIG. 3 illustrates an example bone plate 1200a that is a component of modular bone reinforcement system 1000. FIG. 4 illustrates another example bone plate 1300a that is also a component of modular bone reinforcement system 1000. FIG. 5 illustrates another example bone plate 1300c that is also a component of modular bone reinforcement system 1000.

Modular bone reinforcement system 1000 includes a plurality of bone plates 1100. Each bone plate of the plurality of bone plates 1000 has a series of tabs disposed along at least one edge of the bone plate for forming a snap-fit attachment to a mating series of tabs of another bone plate of the plurality of bone plates. Thus, the snap-fit attachment is formed by an interlocking structural engagement of two series of tabs defined by adjacent bone plates of a modular bone reinforcement system and creates an assembled bone reinforcement. Each bone plate of the plurality of bone plates 1000 can have multiple series of tabs disposed along multiple edges of the respective bone plate, allowing individual bone plates to be connected to more than one adjacent bone plate through the snap fit attachments formed between mating series of tabs.

Attachments between bone plates of the modular bone reinforcement system 1000 can be formed before, during, or after placement on a bone as part of a method of reinforcing a bone, as described below. The snap fit attachment formed between individual bone plates of the modular bone reinforcement system 1000 is a dynamic attachment, permitting adjustment of a bone reinforcement that is assembled as the snap fit attachments are formed by rotational movement of one or both bone plates forming a particular attachment about an axis extending through the attachment formed between the interlocking series of tabs of the two attached bone plates. As an example, FIG. 1 illustrates assembled bone reinforcement 1050 in a first configuration while FIG. 2 illustrates assembled bone reinforcement 1050 in a second configuration. To transition the assembled bone reinforcement 1050 from the first configuration to the second configuration, bone plates 1200b, 1200d, 1200e have been rotated upward along the axis of the respective snap fit attachment 1250a, 1250b, 1250c formed with bone plate 1200. The dynamic nature of snap fit attachments 1250a, 1250b, 1250c enable this transition between structural configurations of the assembled bone reinforcement 1050 and, as such, permits such transition between structural configurations after assembly of a bone reinforcement. It is noted, though, that the mating series of tabs of the individual bone plates of the modular bone reinforcement system permit the formation of snap fit attachments that position individual bone plates in desired positions upon formation of a snap fit attachment between the bone plates, eliminating the need for transition between structural configurations after assembly of a bone reinforcement.

A modular bone reinforcement system according to a particular embodiment can have any suitable number of individual bone plates and a skilled artisan will be able to select an appropriate number of individual bone plates for a modular bone reinforcement system according to a particular embodiment based on various considerations, including any dimensions of a bone surface onto which attachment of an assembled bone reinforcement is desired. Non-limiting examples of suitable number of bones plates for inclusion in modular bone reinforcement systems include two, more than two, three, a plurality, four, five, six, ten, more than ten, twelve, and more than twelve bone plates. As illustrated in FIGS. 1 and 2, modular bone reinforcement system 1000 includes nine individual bone plates 1200a, 1200b, 1200c, 1200d, 1200e, 1300a, 1300b, 1300c, and 1300d.

Individual bone plates can have any suitable shape and configuration and a skilled artisan will be able to select an appropriate shape and configuration for a bone plate according to a particular embodiment, and for inclusion in a modular bone reinforcement system according to a particular embodiment, based on various considerations, including the topography of a particular portion of a bone surface onto which attachment of an assembled bone reinforcement that includes the individual bone plate is desired. Non-limiting examples of suitable shapes include square, rectangular, triangular, circular, ovoid, and other shapes. The shape selected for a particular bone plate need only have an edge that defines a series of tabs suitable for forming the snap-fit attachments described herein. One example configuration includes a shape having multiple edges, such as a square or a triangle, with a series of tabs formed on at least one of the edges and with another of the edges being free of tabs or other attachment structures. Another example configuration includes a shape having multiple edges, such as a square or a triangle, with a series of tabs formed on at least two of the edges. Another example configuration includes a shape having multiple edges with each edge of the multiple edges defining a series of tabs. Also, individual bone plates can have any suitable three-dimensional configuration, and flat planar plates are only an example of a suitable three-dimensional configuration. Other examples of suitable three-dimensional configurations for bone plates according to embodiments include, but are not limited to, curved planar configurations, and scutoid configurations.

As best illustrated in FIG. 3, bone plate 1200a has a main body 1210a having a square shape and defining edges 1212a, 1214a, 1216a, and 1218a. Edge 1212a defines series of tabs 1222a. Edge 1214a defines series of tabs 1224a. Edge 1216a defines series of tabs 1226a. Edge 1218a defines series of tabs 1228a. Main body 1210a has upper surface 1230a and opposing lower surface 1232a and defines a plurality of passageways 1240a. Each passageway 1242a, 1244a, 1246a, 1248a of the plurality of passageways 1240a extends through the entire thickness of the main body 1210a, from the upper surface 1230a to the lower surface 1232a and provides structure for receiving or guiding a reduction device, such as a bone screw, a temporary fixation device, such as a Kirschner wire (K-wire), a drug delivery device, such as a needle, a sensor, a clamp attachment, an additive fixation member, or other suitable ancillary device.

As best illustrated in FIG. 4, bone plate 1300a has a triangular shape. As such, bone plate 1300a has a main body 1310a having a triangular shape and defining edges 1312a, 1314a, and 1316a. Edge 1312a defines series of tabs 1322a. Edge 1314a defines series of tabs 1324a. Edge 1316a defines series of tabs 1326a. Main body 1310a has upper surface 1330a and opposing lower surface 1332a and defines a single central passageway 1340a that extends through the entire thickness of the main body 1310a, from the upper surface 1330a to the lower surface 1332a and provides structure for receiving or guiding a reduction device, such as a bone screw, a temporary fixation device, such as a Kirschner wire (K-wire) or equivalent, a drug delivery device, such as a needle, a sensor, a clamp attachment, an additive fixation member, or other suitable ancillary device.

Bone plate 1300c is similar to bone plate 1300a, except as described below. Thus, as best illustrated in FIG. 5, bone plate 1300c has a triangular shape. As such, bone plate 1300c has a main body 1310c having a triangular shape and defining edges 1312c, 1314c, and 1316c. Edge 1312c defines series of tabs 1322c. Edge 1314c defines series of tabs 1324c. Edge 1316c defines series of tabs 1326c. Main body 1310c has upper surface 1330c and opposing lower surface 1332c. In this example bone plate 1300c, upper surface 1330c defines a plurality of ridges 1350c that extend away from the upper surface 1330c and provide structure onto which another element, such as a navigation extension including a tracker array for use with a robotic and/or augmented reality equipment, or other device, can be temporarily or permanently attached. Such additional elements can be included in a modular bone reinforcement system according to an embodiment, if desired.

Bone plates can define additional structures to facilitate additional aspects of the process of securing an assembled bone reinforcement to a bone. For example, bone plates can define additional passageways through which bone cement or void filler can be passed. Furthermore, additional components can be included to enhance the snap-fit attachment formed between bone plates, such as a pin that extends through the interlocking series of tabs from two adjacent, and connected, bone plates. Also, bone plates can define through holes for bone screws to allow passage of dynamic and/or compression screws to generate compressive forces across surfaces to which the plates are placed, such as across fracture gaps. Inclusion of screw holes, and use of screws with individual bone plates, is considered advantageous at least because it provides additional load-bearing and load-sharing properties.

Modular bone reinforcement systems according to particular embodiments can include additional components useful in the securement of a bone reinforcement assembled using the bone plates of the modular bone reinforcement system to a bone. For example, a modular bone reinforcement system can include one or more bone screws and one or more temporary fixation devices, such as a Kirschner wire (K-wire) or equivalent. Also, modular bone reinforcement systems can include additional components useful in the installation of a bone reinforcement assembled using the bone plates of the modular bone reinforcement on a bone. For example, a clamp or navigation extension useful with navigation systems in identifying the location of the bone plate(s) during placement and securement to bone can be included in a modular bone reinforcement system according to an embodiment, if desired.

Bone plates of the modular bone reinforcement systems can be connected to each other in any suitable pattern or arrangement during assembly of a bone reinforcement. A skilled artisan will be able to select an appropriate pattern or arrangement before or during assembly of a bone reinforcement based on various considerations, including the available space, the topology of the bone surface being reinforced, and any anatomical features of the bone surface or other body components that need to be accommodated. The modularity of the inventive systems enable creation of a wide variety of patterns and arrangements in the assembly of an assembled bone reinforcement, from simple straight-chain like arrangements, to zig-zag formations, to tessellations that can cover a relatively large and topologically complex bone surface. The inclusion of bone plates of various sizes, shapes, and/or configurations in a modular bone reinforcement system is considered advantageous at least because it expands the range of patterns and arrangements that can be made with a modular bone reinforcement system according to a particular embodiment. Furthermore, the interlocking structures enable the creation of non-overlapping patterns that most efficiently cover a surface, such as tessellations, including Voronoi tessellations.

Figure 6:
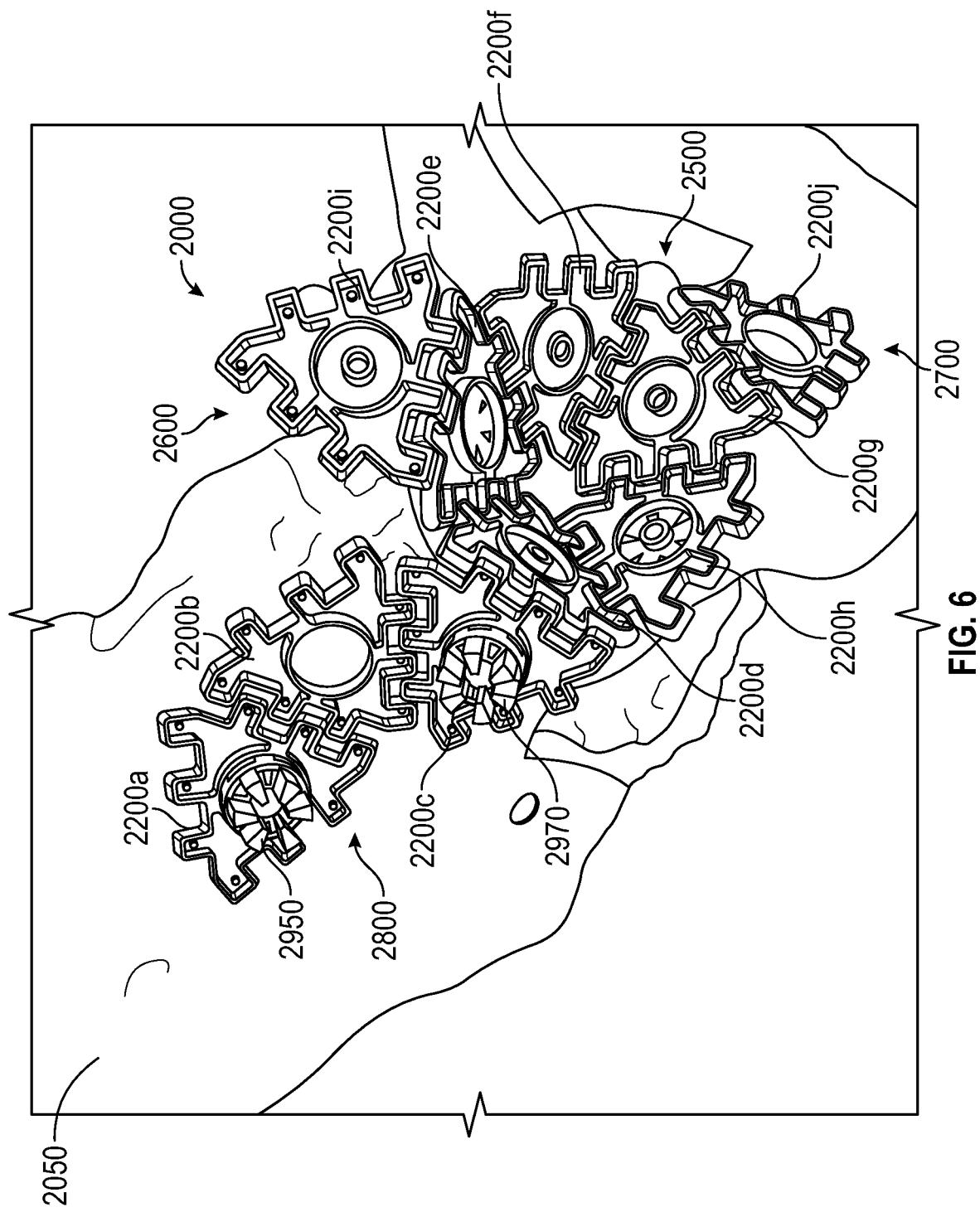
FIG. 6 illustrates an example assembled bone reinforcement secured to a bone.

FIG. 6 illustrates an example assembled bone reinforcement 2000. The assembled bone reinforcement 2000 is secured to a bone 2050. The assembled bone reinforcement 2000 includes ten bone plates 2200a, 2200b, 2200c, 2200d, 2200e, 2200f, 2200g, 2200h, 2200i, and 2200j, each of which has a triangular shape with a series of tabs formed on each of the three edges of the individual bone plate. The assembled bone reinforcement 2000 includes a cup portion 2500 and first 2600, second 2700, and third 2800 extension portions, each of which extends away from a peripheral edge of cup portion 2500. Each of first 2600 and second 2700 extension portions include a single bone plate, while third extension portion 2800 includes three bone plates 2200a, 2200b, 2200c connected to each other. A first bone screw 2950 is disposed through a passageway in bone plate 2200a and a second bone screw 2970 is disposed through a passageway in bone plate 2200c, securing the assembled bone reinforcement 2000 to bone 2050. Cup portion 2500 is disposed in a recess of the bone, such as the acetabulum of a hip bone.

Figure 7:
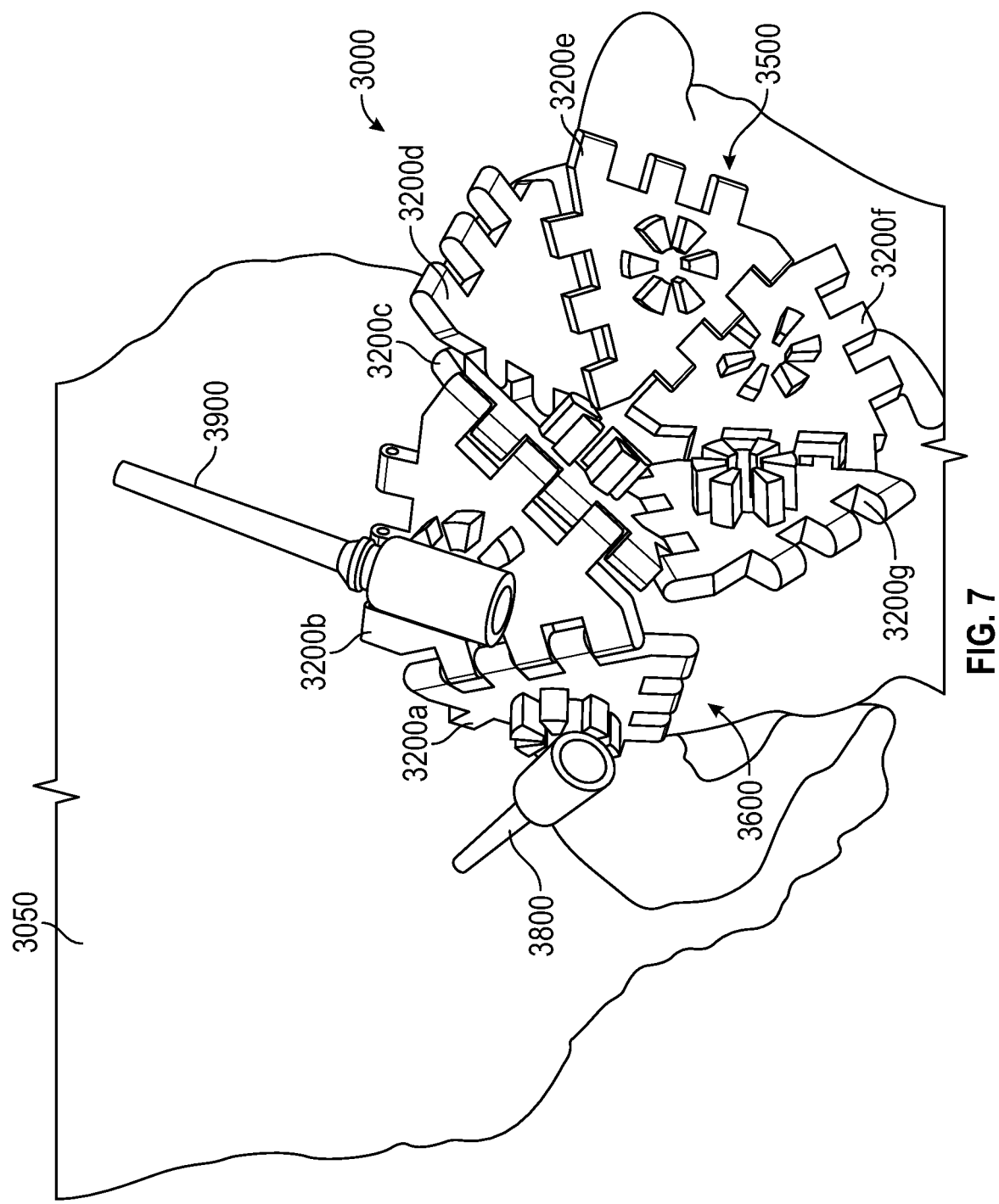
FIG. 7 illustrates another example assembled bone reinforcement disposed on a bone. First and second navigation extensions are attached to individual bone plates of the assembled bone reinforcement.

FIG. 7 illustrates another example assembled bone reinforcement 3000. The assembled bone reinforcement 3000 is disposed on a bone 3050. The assembled bone reinforcement 3000 includes seven bone plates, 3200a, 3200b, 3200c, 3200d, 3200e, 3200f, and 3200g, each of which has a triangular shape with a series of tabs formed on each of the three edges of the individual bone plate. The assembled bone reinforcement 3000 includes a cup portion 3500 and an extension portion 3600 that extends away from a peripheral edge of cup portion 3500. Cup portion 3500 is disposed in a recess of the bone, such as the acetabulum of a hip bone. First 3800 and second 3900 navigation extensions are attached to ridges 3250a, 3250b that extend away from the upper surface 3230a, 3230b of the respective individual bone plate 3200a, 3200b of the assembled bone reinforcement 3000.

Figure 8:
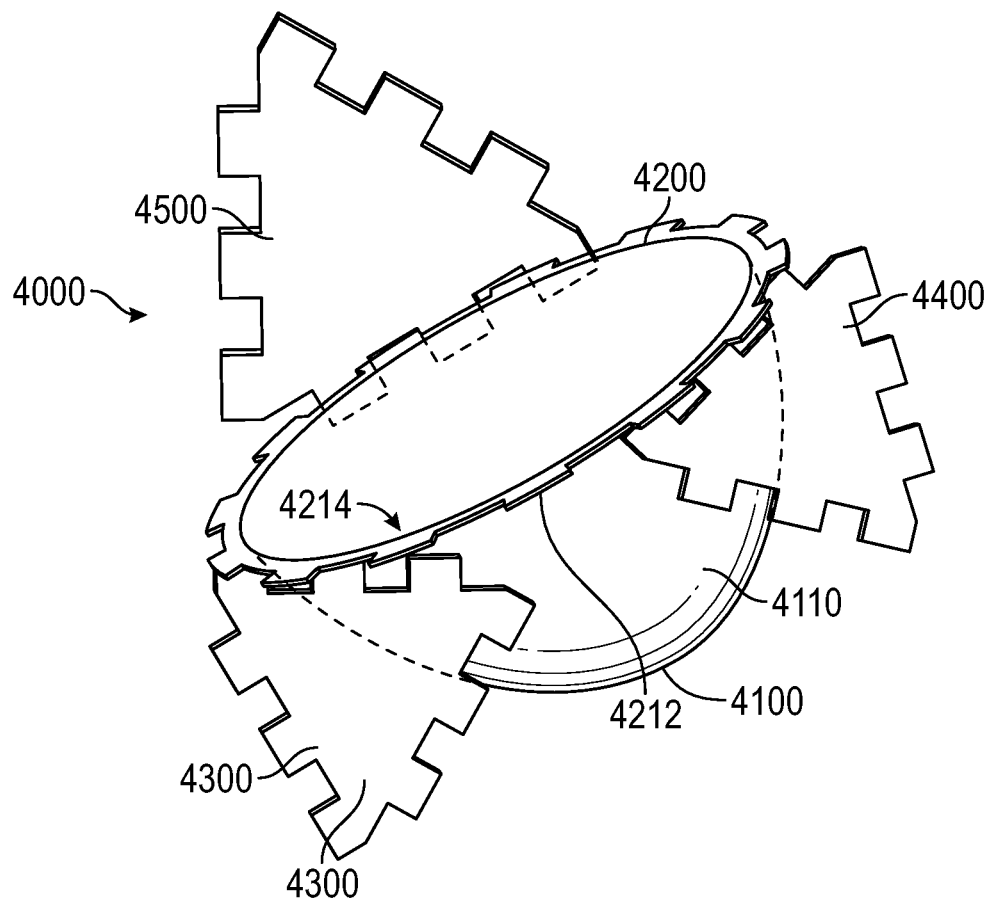
FIG. 8 is a perspective view of an example assembled bone reinforcement useful as an acetabular cup with extensions for revision hip surgery.
Figure 9:
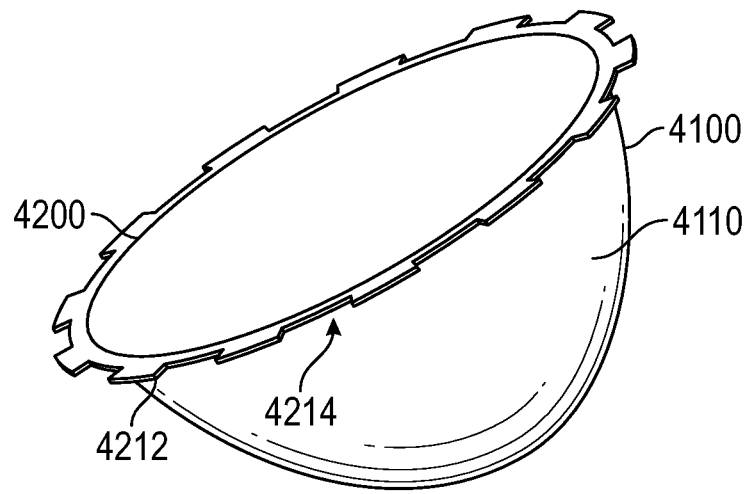
FIG. 9 is a perspective view of the liner and shell components of the assembled bone reinforcement illustrated in FIG. 8.

FIG. 8 illustrates another example assembled bone reinforcement 4000. The assembled bone reinforcement 4000 is adapted for use as an acetabular cup with extensions for revision hip surgery. The assembled bone reinforcement 4000 includes a shell 4100 having an outer surface 4110 and defining an inner recess 4112. A liner 4200 is sized and configured to snap-fit into the inner recess 4112 of the shell 4100. The liner 4200 has an outer surface 4210 and a peripheral edge 4212 that defines a series of tabs 4214. As best illustrated in FIG. 9, the liner 4200 is positioned such that the peripheral edge 4212, and its series of tabs 4214, extend axially and radially beyond the outer surface 4110 of the shell 4100 when snap-fit into the inner recess 4112 of the shell 4100. This positioning makes the series of tabs 4214 available for forming snap-fit attachments with bone plates 4300, 4400, 4500. Attached to the liner 4200 in this manner, bone plates 4300, 4400, 4500 are available as extensions of the assembled acetabular cup and can be used to secure the assembled bone reinforcement to a bone, such as with an appropriate bone screw or other means.

Figure 10:
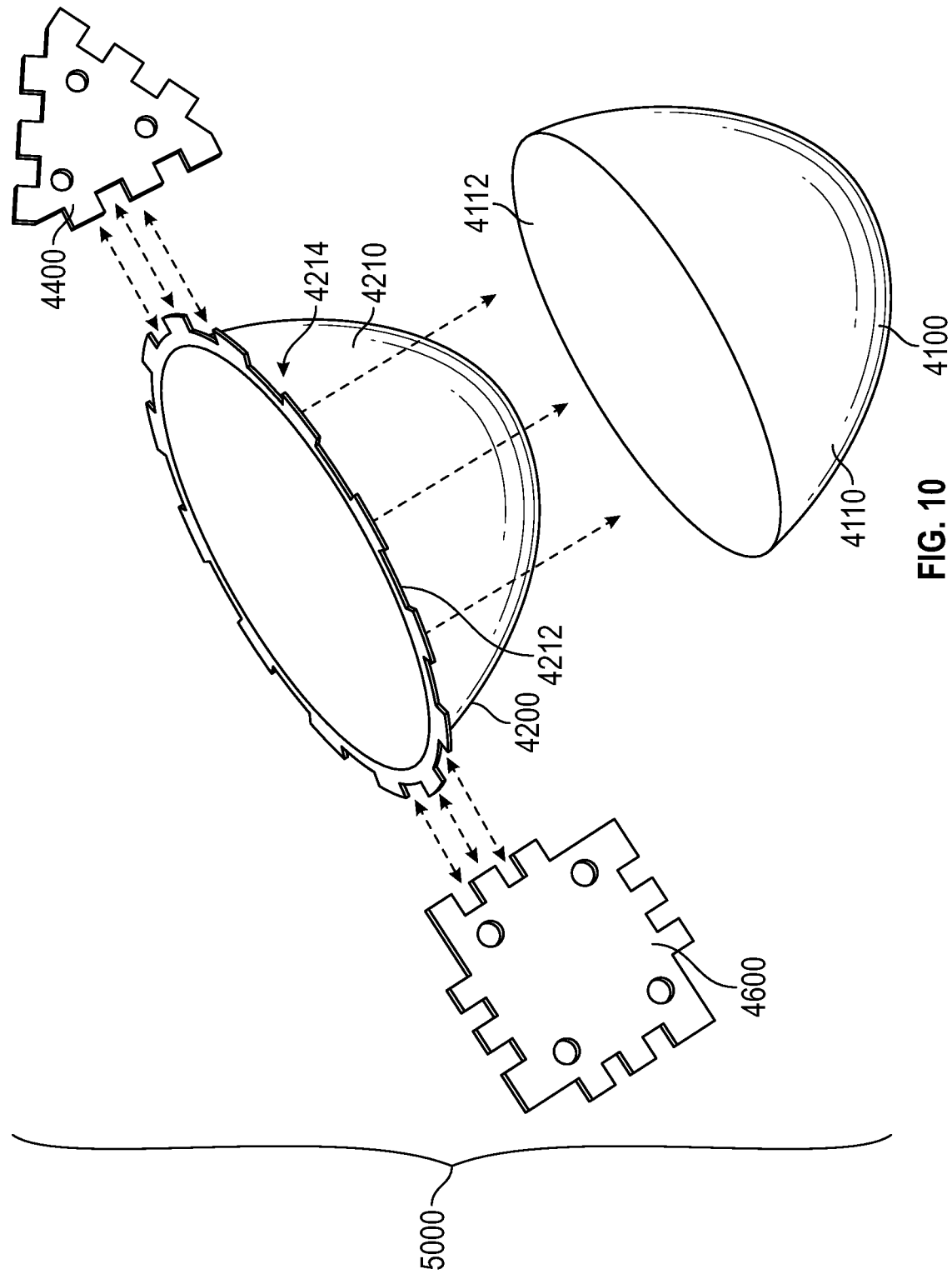
FIG. 10 is a perspective view of a bone reinforcement system that can be used to form the assembled bone reinforcement illustrated in FIG. 8.

FIG. 10 is a perspective view of a bone reinforcement system 5000 that can be used to form the assembled bone reinforcement 4000 illustrated in FIG. 8. The bone reinforcement system 5000 includes shell 4100, liner 4200, plates 4300 (omitted from FIG. 10 for simplicity), 4400, 4500 (omitted from FIG. 10 for simplicity), and additional plate 4600, which has a shape different from plates 4300, 4400, and 4500.

Figure 11:
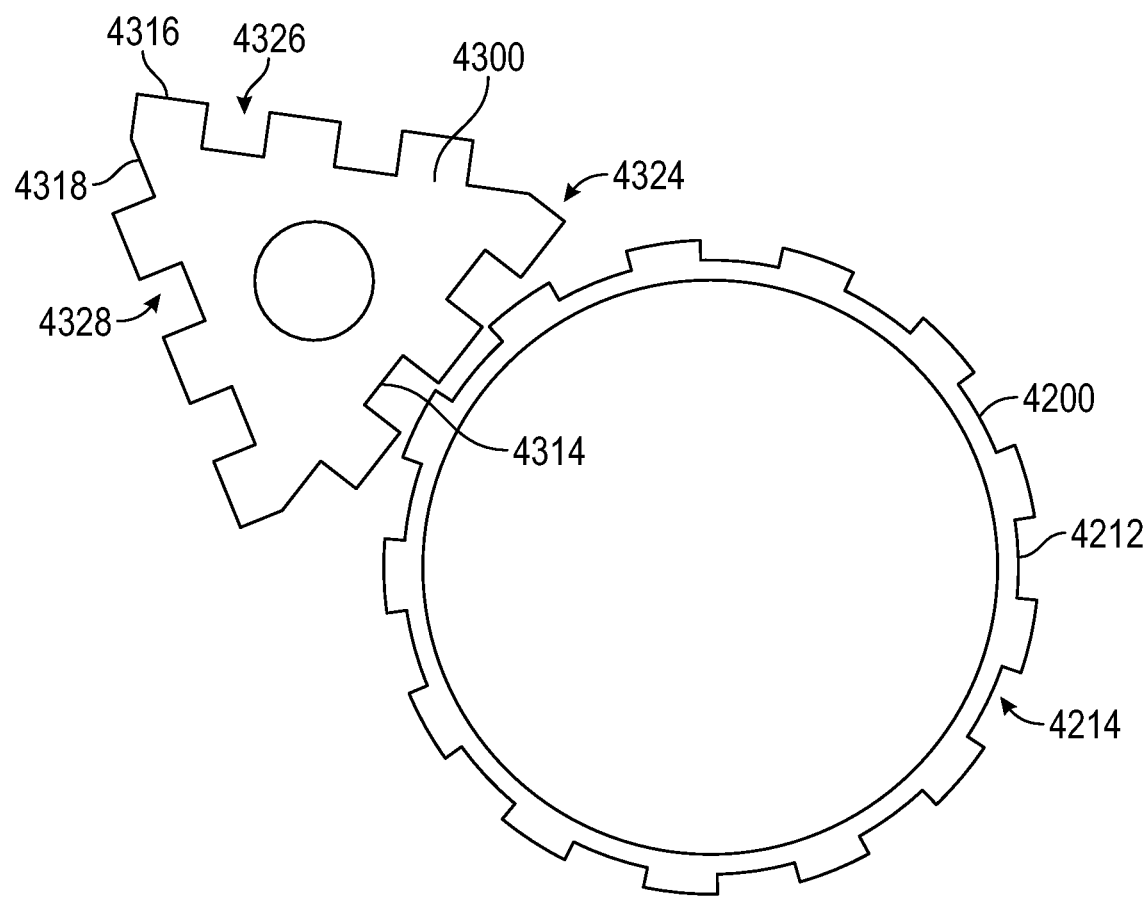
FIG. 11 is a top view of the liner component and one of the bone plates of the bone reinforcement system illustrated in FIG. 10.

FIG. 11 is a top view of the liner 4200 and bone plate 4300. Peripheral edge 4212 of liner 4200 defines a series of tabs 4214 that extends around the entire circumference of the liner 4200. Bone plate 4300 defines a series of tabs 4324 on one edge 4314 that extends along a curvilinear path that is complimentary to the circumference of the liner 4200, enabling a snap-fit connection between the liner 4200 and the bone plate 4300 along any portion of the peripheral edge 4212 of the liner 4200. Each of the other edges 4316, 4318 of the bone plate 4300 extends along a linear path and defines a series of tabs 4326, 4328. As such, series of tabs 4326, 4328 extend along a linear path, in contrast to the curvilinear path of series of tabs 4324. This structural configuration of series of tabs 4326, 4328 facilitates connection of bone plate 4300 to additional bone plates having series of tabs configured in this manner.

Figure 12:
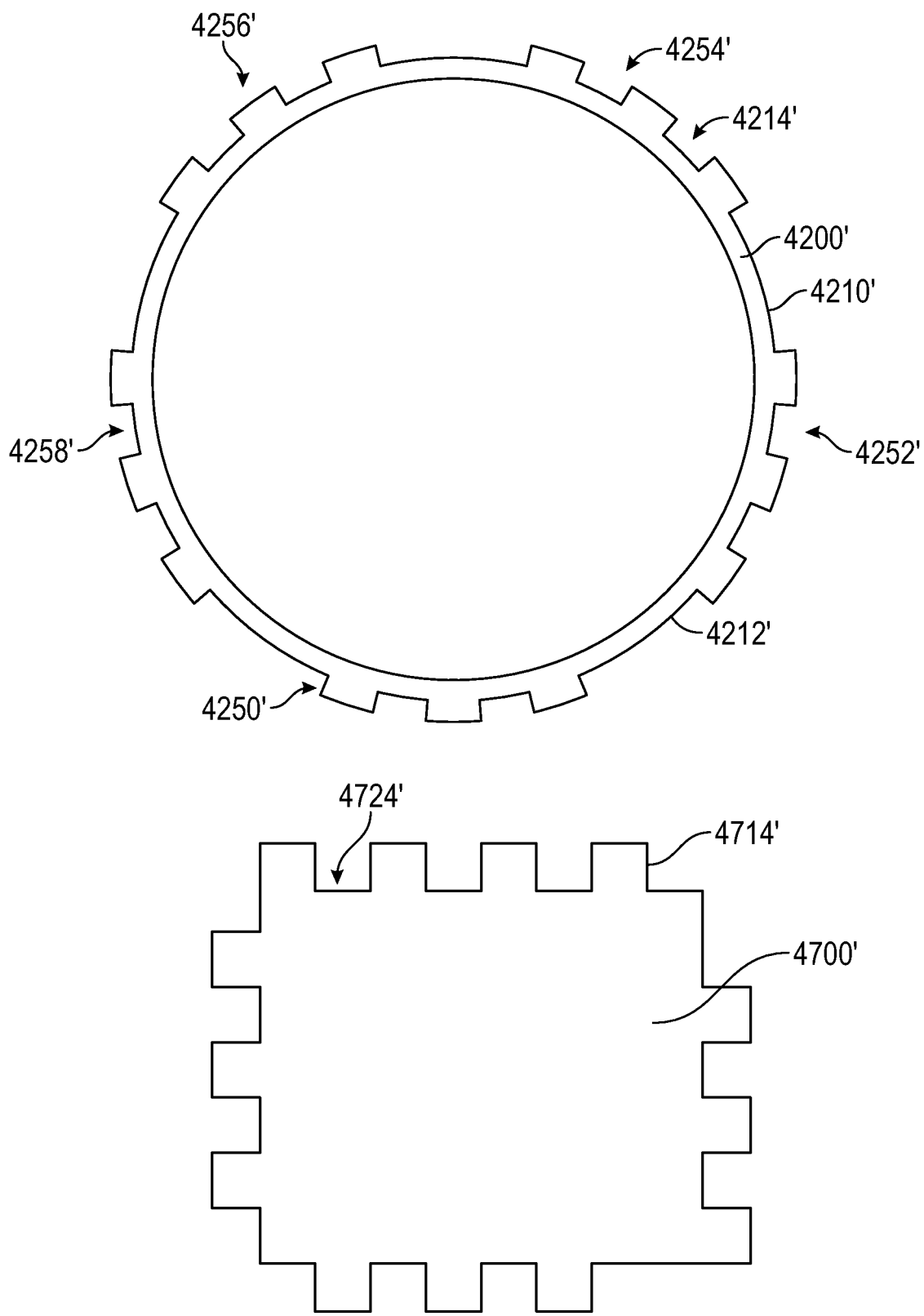
FIG. 12 is a top view of an alternative liner component and one of the bone plates of the bone reinforcement system illustrated in FIG. 10.

FIG. 12 is a top view of an alternative liner 4200' and an alternative bone plate 4700' for inclusion in the bone reinforcement system 5000 illustrated in FIG. 10. Liner 4200' is similar to liner 4200, except as detailed below. Thus, liner 4200' is sized and configured to snap-fit into the inner recess 4112 of the shell 4100 and has an outer surface 4210' and a peripheral edge 4212' that defines a series of tabs 4214'. In contrast to the series of tabs 4214 that extend continuously along the peripheral edge 4212 of liner 4200, peripheral edge 4212' of liner 4200' defines discrete series of tabs 4250', 4252', 4254', 4256', 4258'. Series of tabs 4250' extends along a linear path such that the series of tabs 4250' is configured to snap-fit with a series of tabs 4724' extending along a linear path of an edge 4714' of bone plate 4700'. Each of the remaining series of tabs 4252', 4254', 4256', 4258' extends along a curvilinear path defined by the peripheral edge 4212' of the liner 4200', making series of tabs 4252', 4254', 4256', 4258' suitable for snap-fit attachment to a bone plate defining a complimentary series of tabs extending along a complimentary curvilinear path, such as bone plate 4300.

While individual bone plates in the examples described above have planar structural configurations, assembling individual bone plates into assembled bone reinforcements provides other structural configurations, including multi-planar configurations, that can be useful for a variety of reinforcement purposes, including surface reinforcement, space-filling, fracture spanning, and the like, and in a variety of clinical situations. For example, FIG. 13 illustrates an example assembled bone reinforcement 5200a that includes seven individual bone plates 5201, 5202, 5203, 5204, 5205, 5206, 5207. The assembled bone reinforcement 5200a includes a number of triangular bone plates 5201, 5204, 5205, 5207 and non-triangular bone plates 5202, 5203, 5206. The non-triangular bone plates 5202, 5203, 5206 advantageously have a quadrilateral configuration, such as a square, but can have other suitable configurations, if desired. Each bone plate 5201, 5202, 5203, 5204, 5205, 5206, 5207 includes pairs of tabs, as described above, that provide structure for interlocking with additional bone plates to add to the assembled bone reinforcement 5200a if needed or desired.

FIG. 14 illustrates another assembled bone reinforcement 5500, which is a super structure that includes the assembled bone reinforcement 5200a illustrated in FIG. 13 and four additional, and identical, individual assembled bone reinforcements 5200b, 5200c, 5200d, 5200e, each of which has the same multi-planar structural configuration of assembled bone reinforcement 5200a as illustrated in FIG. 13 and described above.

Figure 15:
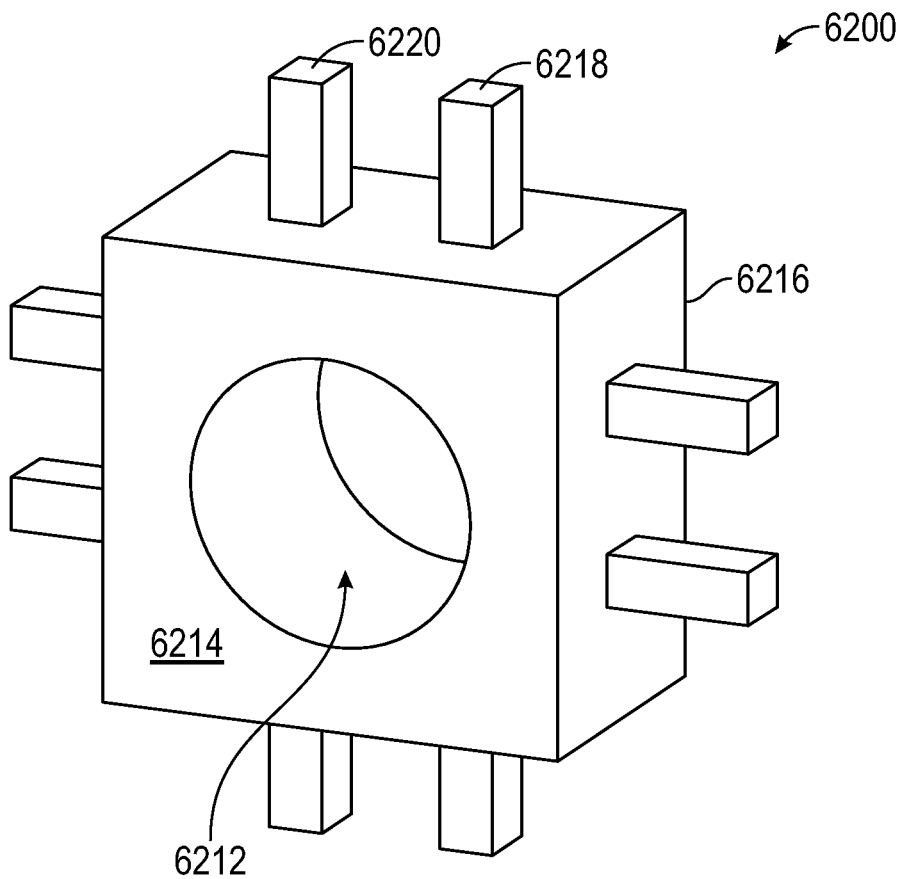
FIG. 15 is a perspective view of another example bone plate.

FIG. 15 illustrates another example bone plate 6200. The bone plate 6200 has a cuboid configuration 6210 with six quadrilateral facets and a passageway 6212 extending through the bone plate 6200 from one side 6214 to an opposite side 6216. Pairs of tabs 6218, 6220 extend away from multiple facets of the bone plate 6200 and provide structure for interlocking with additional bone plates to form an assembled bone reinforcement. All components of modular bone reinforcement systems, bone plates, and assembled bone reinforcements can be formed of any suitable material or a combination of materials. Examples of suitable materials include materials conventionally used in implantable bone reinforcement and securement devices, such as metals, polymeric materials, biocomposites, and combinations of these materials. Examples of suitable metals include elemental metals, such as titanium, and alloys, such as stainless steel, nickel titanium (e.g., Nitinol), and cobalt chromium. Examples of suitable polymeric materials include plastics, such as polyether ether ketone (PEEK), polyethylene, and ultra-high molecular weight polyethylene, and elastomers, such as polyurethane. Combinations of these materials can also be used. Relatively flexible materials are considered advantageous as the flexibility of these materials further enable shaping a bone plate and/or an assembled bone reinforcement to the topology at a particular location at which a reinforcement is being made using the bone plate and/or assembled bone reinforcement. Also, multiple planar bone plates can be assembled into an assembled bone reinforcement that has a faceted structure to simulate curved surfaces.

All components of modular bone reinforcement systems, bone plates, and assembled bone reinforcements can be made using any suitable technique and/or process, including additive manufacturing, 3D printing, molding, machining, and other suitable fabrication processes.

All components of modular bone reinforcement systems, bone plates, and assembled bone reinforcements according to embodiments of the invention can have any suitable surface treatment, including surface treatments conventional for bone plates and implantable orthopedic medical devices, such as surface roughening.

The modular bone reinforcement systems, bone plates, and assembled bone reinforcements according to the invention are useful in a variety of clinical applications and environments in which reinforcement of a bone structure is necessary or desired. For example, as best illustrated in FIGS. 6 and 7, bone reinforcements can be assembled from modular bone reinforcement systems that accommodate difficult three-dimensional topology of challenging environments, such as the hip bone, bones in the knee, and vertebrae, for example. Specific clinical applications contemplated include trauma applications, such on long bones, in periarticular locations, and voids in bones; bone reduction techniques, such as provisional/temporary fixation in fracture fixation/reduction; spinal applications, such as use as an adjunctive positioning with intervertebral spacers, cages, and/or pedicle fixation; periprosthetic fractures, such as total hip replacements, total knee replacements, and trochanteric claw plates; small bone applications, such as hand, foot, and ankle applications; craniomaxillofacial applications, and pediatric applications. The configurability of the modular bone reinforcement systems, bone plates, and assembled bone reinforcements according to the invention make them particularly well suited for knee reinforcement, ankle reinforcement, spinal reinforcement, and various other reinforcement efforts. As such, the modular bone reinforcement systems, bone plates, and assembled bone reinforcements are useful in orthopedic surgery, trauma surgery, revision arthroplasty, craniomaxillofacial surgery, and other procedures.

The invention also includes methods of reinforcing a bone. The methods utilize one or more of the modular bone reinforcement systems, bone plates, and assembled bone reinforcements according to the invention.

Figure 16:
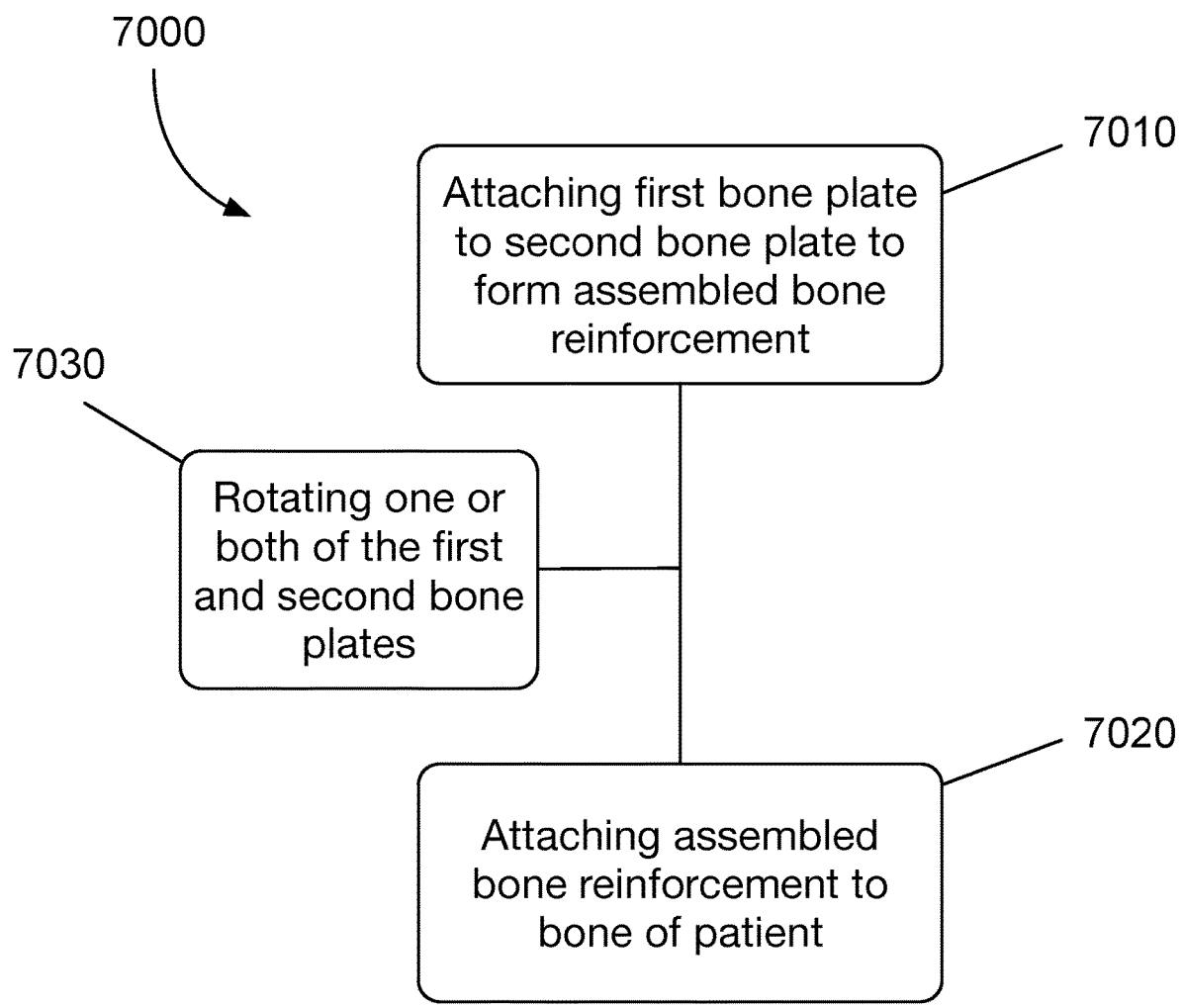
FIG. 16 is a flowchart representation of an example method of reinforcing a bone.

FIG. 16 illustrates an example method of reinforcing a bone 7000. An initial step 7010 comprises attaching a first bone plate of a modular bone reinforcement system according to an embodiment to a second bone plate of the modular bone reinforcement system to form an assembled bone reinforcement. This step 7010 can be accomplished by forming a snap-fit attachment between first and second bone plates of the modular bone reinforcement system by interlocking the series of tabs on the respective bone plates. Another step 7020 comprises attaching the assembled bone reinforcement to a bone of a patient, such as a bone of a human being. This step 7020 can be accomplished using one or more suitable bone fixation apparatuses and techniques, such as a bone screw, K-wire, or both. An optional step 7030 comprises rotating one or both of the first and second bone plates about an axis extending through the attachment formed between the interlocking series of tabs of the first and second attached bone plates. If included, step 7030 can be performed after step 7010 is completed and before step 7020 is initiated. Alternatively, step 7030 can be performed after step 7010 is completed and while step 7020 is being performed, or after step 7020 is completed. Inclusion of this step 7030 is considered advantageous at least because it enables configuring the assembled bone reinforcement to mimic or extend along the surface of the bone at a location at which the assembled bone reinforcement is attached or will be attached.

Figure 17:
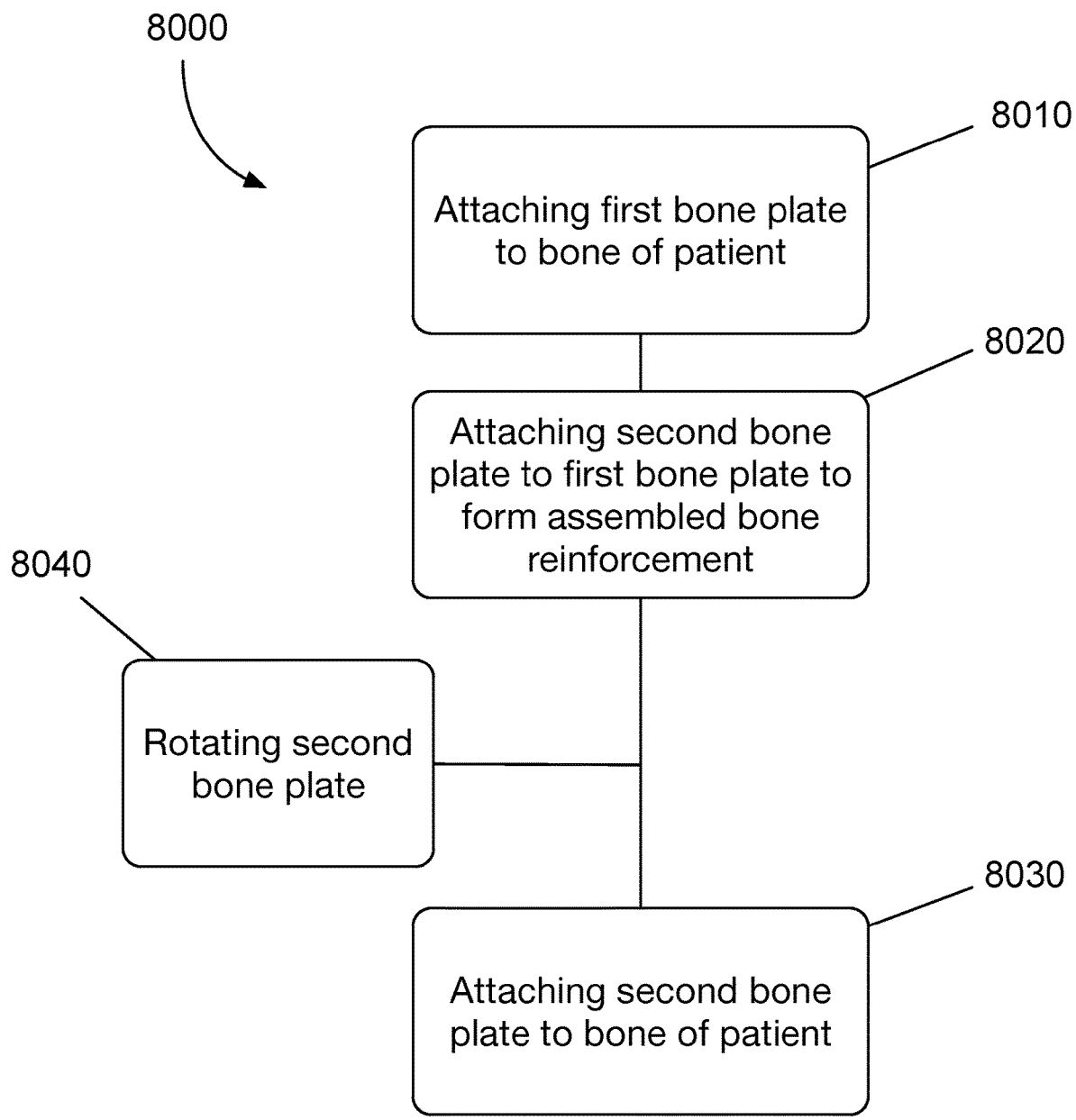
FIG. 17 is a flowchart representation of another example method of reinforcing a bone.

FIG. 17 illustrates another example method of reinforcing a bone 8000. An initial step 8010 comprises attaching a first bone plate of a modular bone reinforcement system according to an embodiment to a bone of a patient, such as a bone of a human being. This step 8010 can be accomplished using one or more suitable bone fixation apparatuses and techniques, such as a bone screw, K-wire, or both. Another step 8020 comprises attaching a second bone plate of the modular bone reinforcement system to the first bone plate to form an assembled bone reinforcement. This step 8020 can be accomplished by forming a snap-fit attachment between the first and second bone plates of the modular bone reinforcement system by interlocking the series of tabs on the respective bone plates. Another step 8030 comprises attaching the second bone plate to the bone. This step 8030 can be accomplished using one or more suitable bone fixation apparatuses and techniques, such as a bone screw, K-wire, or both. An optional step 8040 comprises rotating the second bone plate about an axis extending through the attachment formed between the interlocking series of tabs of the first and second attached bone plates. If included, step 8040 is performed after step 8020 is completed and before step 8030 is initiated. Alternatively, step 8040 can be performed after step 8020 is completed and while step 8030 is being performed. Inclusion of this step 8030 is considered advantageous at least because it enables configuring the assembled bone reinforcement to mimic or extend along the surface of the bone at a location at which the assembled bone reinforcement is attached or will be attached.

Those with ordinary skill in the art will appreciate that various modifications and alternatives for the described and illustrated example embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A modular bone reinforcement system, comprising
a shell defining an inner recess;
a liner configured to be snap-fit into the inner recess of the shell, the liner defining a peripheral edge having a first liner series of tabs extending axially beyond the shell and radially outward from the peripheral edge of the liner;
a first bone plate having at least one first bone plate edge and at least one first bone plate series of tabs disposed along the at least one first bone plate edge; and
a second bone plate having at least one second bone plate edge and at least one second bone plate series of tabs disposed along the at least one second bone plate edge;
wherein the at least one first bone plate series of tabs is adapted to form a first snap-fit attachment with the first liner series of tabs and a second snap-fit attachment with the at least one second bone plate series of tabs.

2. The modular bone reinforcement system of claim 1, wherein the first bone plate has a first shape and the second bone plate has a second shape; and
wherein the first shape and the second shape are different.

3. The modular bone reinforcement system of claim 2, wherein the first shape is triangular.

4. The modular bone reinforcement system of claim 3, wherein the second shape is rectangular.

5. The modular bone reinforcement system of claim 4, wherein the second shape is square.

6. The modular bone reinforcement system of claim 1, wherein the first bone plate has a first shape and the second bone plate has a second shape; and
wherein the first shape and the second shape are the same.

7. The modular bone reinforcement system of claim 6, wherein the first shape and the second shape are triangular.

8. The modular bone reinforcement system of claim 6, wherein the first shape and the second shape are rectangular.

9. The modular bone reinforcement system of claim 8, wherein the first shape and the second shape are square.

10. The modular bone reinforcement system of claim 1, wherein the first liner series of tabs extends along the entire circumference of the peripheral edge of the liner.

11. The modular bone reinforcement system of claim 1, wherein the first liner series of tabs extends along a first portion of the circumference of the peripheral edge of the liner.

12. The modular bone reinforcement system of claim 11, further comprising a second liner series of tabs extending axially beyond the shell and radially outward from the peripheral edge of the liner, the second liner series of tabs extending along a second portion of the circumference of the peripheral edge of the liner and circumferentially spaced from the first liner series of tabs on the peripheral edge of the liner.

13. The modular bone reinforcement system of claim 12, wherein the first bone plate has a second first bone plate edge and a second first bone plate series of tabs disposed along the second first bone plate edge;
wherein the first liner series of tabs extends along a curvilinear path.

14. The modular bone reinforcement system of claim 13, wherein the second first bone plate series of tabs extends along a curvilinear path defined by the second first bone plate edge.

15. The modular bone reinforcement system of claim 14, wherein the second liner series of tabs extends along a linear path.

16. The modular bone reinforcement system of claim 13, wherein the second bone plate series of tabs extends along a linear path defined by the at least one second bone plate edge.

* * * * *